United States Patent
Jung et al.

(10) Patent No.: US 8,956,545 B2
(45) Date of Patent: Feb. 17, 2015

(54) HOLLOW MICRONEEDLE HAVING VARIABLE APPEARANCE AND METHOD FOR MANUFACTURING THE SAME

(75) Inventors: Hyung Il Jung, Chungcheongnam-do (KR); Kwang Lee, Chungcheongnam-do (KR); Sin Kil Cho, Chungcheongnam-do (KR); Young Dook Byeon, Chungcheongnam-do (KR)

(73) Assignee: Incyto Co., Ltd., Chungcheongnam-Do (KR)

( * ) Notice: Subject to any disclaimer, the term of this patent is extended or adjusted under 35 U.S.C. 154(b) by 77 days.

(21) Appl. No.: 13/809,703

(22) PCT Filed: Jul. 8, 2011

(86) PCT No.: PCT/KR2011/005021
§ 371 (c)(1),
(2), (4) Date: Jan. 11, 2013

(87) PCT Pub. No.: WO2012/008716
PCT Pub. Date: Jan. 19, 2012

(65) Prior Publication Data
US 2013/0116523 A1 May 9, 2013

(30) Foreign Application Priority Data
Jul. 12, 2010 (KR) ........................ 10 2010 0066940

(51) Int. Cl.
*C25F 3/00* (2006.01)
*A61M 5/00* (2006.01)
(Continued)

(52) U.S. Cl.
CPC ............ *A61M 5/00* (2013.01); *A61M 37/0015* (2013.01); *A61B 5/14865* (2013.01);
(Continued)

(58) Field of Classification Search
USPC ........................................... 216/11
See application file for complete search history.

(56) References Cited

U.S. PATENT DOCUMENTS 6,783,544 B2    8/2004   Lynch et al.
7,361,307 B2    4/2008   Shartle et al.
(Continued)

FOREIGN PATENT DOCUMENTS

EP    1 695 764    8/2006
JP    2005503194   2/2005
(Continued)

OTHER PUBLICATIONS

Han J.G.E. Gardeniers et al "Silicon Micromachined Hollow Microneedles for Transdermal Liquid Transport," Journal of Microelectromechanical Systems, vol. 12, No. 6, Dec. 2003.
(Continued)

*Primary Examiner* — Roberts Culbert
(74) *Attorney, Agent, or Firm* — Bacon & Thomas, PLLC (57) ABSTRACT

The present invention relates to a method for fabricating a hollow microneedle having a variable appearance. The method makes it possible to vary the length of the microneedle, the outer and inner diameters of the upper and lower parts thereof, the aspect ratio, the sharpness, and the structural bending rate thereof, in accordance with the purposes of the same. Accordingly, the appearance of the hollow microneedles according to the present invention can be varied with flexibility according to various purposes, such as the transferring of medication and the taking of a blood sample, and to various factors, such as the target part for the medication transfer, the depth of the medication transfer, and the amount and viscosity of the medication. Thus, the microneedle can be used as a multi-purpose device for transferring medication.

13 Claims, 6 Drawing Sheets

(51) Int. Cl.
*A61M 37/00* (2006.01)
*A61B 5/1486* (2006.01)
*A61F 9/007* (2006.01)
*B29D 23/00* (2006.01)
*A61K 9/00* (2006.01)
*B81C 1/00* (2006.01)
*B29C 41/08* (2006.01)
*B29C 41/36* (2006.01)
*B29C 41/38* (2006.01)
*G01N 33/49* (2006.01)
*A61B 5/00* (2006.01)
*A61B 5/145* (2006.01)
*B29L 31/00* (2006.01)

(52) U.S. Cl.
CPC ........... *A61F 9/00781* (2013.01); *B29D 23/00* (2013.01); *A61K 9/0021* (2013.01); *B81C 1/00111* (2013.01); *B29C 41/08* (2013.01); *B29C 41/36* (2013.01); *B29C 41/38* (2013.01); *A61M 2037/003* (2013.01); *A61M 2037/0053* (2013.01); *G01N 33/49* (2013.01); *A61B 5/685* (2013.01); *A61B 5/14532* (2013.01); *B81B 2201/055* (2013.01); *B29L 2031/7544* (2013.01)
USPC .......................................................... 216/11

(56) References Cited

U.S. PATENT DOCUMENTS

| 2004/0186419 | A1 | 9/2004 | Cho |
| 2004/0267205 | A1 | 12/2004 | Stemme et al. |
| 2008/0157421 | A1 | 7/2008 | Mukai et al. |
| 2009/0043279 | A1* | 2/2009 | Kaspar et al. ................ 604/506 |

FOREIGN PATENT DOCUMENTS

| KR | 1020040036912 | 5/2004 |
| KR | 1020080074058 | 8/2008 |
| KR | 1020090059971 | 6/2009 |
| WO | 0217985 A2 | 3/2002 |
| WO | 2005049107 A2 | 6/2005 |
| WO | 2006/018642 | 2/2006 |
| WO | 2009072830 A2 | 6/2009 |

OTHER PUBLICATIONS

Shawn P. Davis, et al, "Hollow Metal Microneedles for Insulin Delivery to Diabetic Rats," IEEE Transactions on Biomedical Engineering, vol. 52, No. 5, May 2005.

Wijaya Martanto et al, "Mechanism of fluid infusion during microneedle insertion and retraction," Journal of Controlled Release 112 (2006) 357-361.

Wijaya Martanto et al, Microinfusion Using Hollow Microneedles, Pharmaceutical Research, vol. 23, No. 1, Jan. 2006.

Patrick Griss, et al, "Side-Opened Out-of-Plane Microneedle for Microfluidic Transdermal Liquid Transfer," Journal of Microelectrochemical Systems, 12(3): 296301 (2003).

An extended European Search Report dated Apr. 4, 2014 issued in a corresponding European application No. 11807001.0-1506.

* cited by examiner

FIG.1A

COATING THICKNESS OF 75 μm

FIG.1B

COATING THICKNESS OF 165 μm

FIG.2A

COATING THICKNESS OF 200 μm

FIG.2B

COATING THICKNESS OF 500 μm

FIG. 3A

TEMPERATURE OF 90 DEGREES ℃

FIG. 3B

TEMPERATURE OF 60 DEGREES ℃

FIG. 4A

LIFTING SPEED OF 5 μm/s

FIG. 4B

LIFTING SPEED OF 10 μm/s

FIG.5A

COATING THICKNESS
OF 20 μm/s

FIG.5B

COATING THICKNESS
OF 40 μm/s

FIG.6A

VERTICAL CUTTING
OF UPPER PORTION

FIG.6B

CUTTING OF UPPER PORTION
AT ANGLE OF 60 DEGREES

HOLLOW MICRONEEDLE HAVING VARIABLE APPEARANCE AND METHOD FOR MANUFACTURING THE SAME

TECHNICAL FIELD

The present invention relates to a method for manufacturing a hollow microneedle having a variable appearance and the hollow microneedle manufactured by the same.

BACKGROUND ART

Unlike the existing needles, micronneedles pass through skin without pain and do not leave an external injury. In order to implant a microneedle into skin without pain, a diameter of an upper portion of the microneedle is important for the minimum sharpness. Also, the microneedles needs to pass through a stratum corneum of 10 μm to 20 μm serving as the biggest obstacle in skin, and thus are required to have sufficient physical hardness. However, since the thicknesses and elasticity of skins, efficiency of transdermal drug delivery, the viscosities of drugs, and the amount of administered drugs differ according to species, races, individuals, and skin regions, a method for manufacturing a microneedle having a variable appearance is required.

A hollow silicon microneedle having a bevel angle was developed by Nanopass company in a secondary etching method which is an advanced etching method (WO 0217985; WO 2005049107; Gardeniers, Han J. G. E, et al., Silicon Micromachined Hollow Microneedles for Transdermal Liquid Transport, Journal of microelectro-chemical systems, 12(6): 855-862 (2003)). Griss and Stemme of Stanford University in the USA have proposed a side-opened hollow silicon microneedle and a cross-type hollow silicon microneedle (P. Griss and G. Stemme, Side-Opened Out-of-Plane Microneedles for Microfluidic Transdermal Liquid Transfer, Journal of microelectro-chemical systems, 12(3): 296301 (2003); U.S. Patent Publication No. 2004-0267205).

Prausnitz of Georgia University in the USA proposed a method that forms a mold with a laser and manufactures a hollow microneedle by using deposition and electro-plating (Prausnitz, M. R. et al., Hollow Metal Microneedles for Insulin Delivery to Diabetic Rats IEEE, Transaction on biomedical engineering, 52(5): 909-915 (2005)). However, the hollow microneedle manufactured by the method has problems in diameter and length similarly to the above-described methods. Also, Prausnitz of Georgia University in the USA proposed a new-type hollow glass microneedle that has a bevel angle and a length of about 900 μm formed by lengthening a glass micropipette at a high temperature ("Microinfusion Using Hollow Microneeldes", Pharmaceutical Research, Vol. 23, No. 1, January 2006 and "Mechanism of fluid infusion during microneedle insertion and retraction", Journal of Controlled Release, 2006, 357361). As described above, various hollow microneedles have been developed. However, since the hollow microneedles are manufactured as standardized products to have uniform appearances in length, diameter, aspect ratio, sharpness, and bevel angle, it is difficult for the products of currently standardized hollow microneedles to deliver drugs through various regions of a human body and perform efficient conversion according to drugs having various viscosities, and the medical application of the hollow microneedles are limited compared to the existing hypodermic needle. Therefore, it is continuously required manufacturing technology in which the strength, sharpness, bevel angle, and bending of a hollow microneedle necessary for passing through skin may be adjusted depending on regions of skin, the length of the hollow microneedle may be adjusted according to a degree by which the hollow microneedle passes through skin, and, by adjusting the diameter of the hollow microneedle according to the change in the viscosity and administration amount of treated drug, the external appearance of the hollow microneedle may be flexibly adjusted according to the application method of drug delivery and body material sampling including blood collection.

In the specification, a plurality of papers and patent documents are referenced, and citations thereof are indicated. The overall disclosure of each of the cited paper and patent document is inserted as a reference into the specification, and thus, the level of the technical field of the present invention and the configuration and function of the present invention are clearly described.

DISCLOSURE

Technical Problem

In view of the above, the present invention provides a method for manufacturing a hollow microstructure whose an external appearance (for example, an effective length, an internal diameter and external diameter of an upper portion, a diameter, hardness, sharpness, bevel angle, and aspect ratio of a lower portion, and bending of lower portion) may be varied by adjusting a thickness of a substrate, a diameter of a lifting frame, a lifting speed, a lifting time, a temperature for molding a microneedle, a bevel angle for cutting.

Further, the present invention provides the hollow microstructure, having various external appearances, manufactured by the method.

Technical Solution

In accordance with an aspect of the present invention, there is provided a method for manufacturing a hollow microstructure having a varied appearance, which includes the following operations.

The method includes: (a) coating a solution of a viscous material on a surface of a substrate; (b) bringing the solution of the viscous material into contact with a frame; (c) lifting the substrate, the frame, or the substrate and the frame for the contacted frame and substrate to be spaced apart from each other to thereby manufacture a solid microstructure; (d) depositing metal on the solid microstructure; (e) protecting a top of the metal-deposited solid microstructure, and metal-plating a surface of the microstructure; (f) removing the solid microstructure to obtain a hollow microstructure; (g) manufacturing a microneedle manufactured at a distal end of an injector; and (h) manufacturing a bent microneedle, wherein a coating thickness of the viscous material, a diameter of the frame, a temperature of the viscous material, a lifting speed, a plating thickness, or combination thereof is adjusted.

In accordance with another aspect of the present invention, there is provided a hollow microneedle manufactured by the above-described method of the present invention.

The inventors have made an effort to develop an improved process that can manufacture a hollow microneedle having a variable appearance. As a result, the inventors have realized that a hollow microneedle having characteristics (for example, an effective length, an internal diameter and external diameter of an upper portion, a diameter, hardness, sharpness, bevel angle, and aspect ratio of a lower portion, and bending) that are more simply and quickly adjusted at lower manufacturing cost, when adjusting a coating thickness of a viscous material, a diameter of a frame, a temperature of the viscous material, a lifting speed, and a lifting time, a plating thickness, a cut bevel angle, or combination thereof.

The method of the present invention will be described below in detail by operation.

Operation (a): Coating a Solution of a Viscous Material on a Surface of a Substrate According to the method of the present invention, a solution of a viscous material is first coated on a surface of a substrate, for manufacturing a solid microstructure that is a mold of a hollow microneedle.

A material, used for manufacturing the solid microstructure that is the mold of the hollow microneedle, is a viscous material. In the specification, the term "viscous material" denotes a material that has a fluid type which has low viscosity at a certain temperature or higher but, when approaching a glass transition temperature by lowering the certain temperature, has high viscosity. A viscous material, used in the specification, includes an acryl-based polymer, an amide-based polymer, an acetyl-based polymer, a vinyl-based polymer, an epoxy-based polymer, a silicon-based polymer, a sulfonic resin, a polycarbonate-based polymer, or a copolymer thereof, but is not limited thereto. All viscous materials which are commonly used in the art may be used.

The viscous material used in the specification has viscosity when the viscous material becomes a fluid. The viscosity may be variously changed according to the kind, concentration, and temperature of viscous material and an organic solvent, and may be adjusted to be suitable for the purpose of the present invention. When the viscous material of the present invention becomes a fluid, the viscous material has viscosity of 200,000 cSt or less.

Changing a viscous material to a fluid may be performed by various methods known in the art. For example, when a viscous material is a liquid polymer, an operation of changing the viscous material to a fluid is not needed. When a viscous material is a thermoplastic resin, by heating the viscous material at a temperature equal to or higher than a melting point and then lowering the temperature to approach the glass transition temperature, the viscous material has viscosity. Also, by dissolving a viscous material in a suitable organic solvent (for example, anhydrous or hydrous low alcohol of 1-4 carbon atoms, acetone, ethyl acetate, chloroform, 1,3-butylene glycol, hexane, diethyl ether, butyl acetate, etc.), the viscous material may become a fluid.

In the specification, the term "coating" denotes that a layer of a specific material having a certain thickness is formed on a target surface. A substrate providing a surface is formed of polymer, organic chemical material, metal, ceramic, semiconductor, or the like.

According to an implementation example of the present invention, a coating thickness of a solution of a viscous material used in the present invention may be adjusted within a range from 10 μm to 500 μm, a range from 50 μm to 200 μm, or a range from 75 μm to 165 μm. The coating thickness affects various appearance factors (i.e., an effective length, an internal diameter, an external diameter, sharpness, an aspect ratio, etc.) of a finally manufactured hollow microneedle, and particularly, acts as a variable that changes an effective length, diameter, and sharpness of a solid microneedle, namely, an effective length, sharpness, external diameter, and internal diameter of a hollow microneedle. In the range of the coating thickness, as a coating thickness increases, an external diameter and internal diameter of a hollow microneedle increase, an effective length increases, and sharpness decreases.

According to an implementation example of the present invention, a viscous material used in the present invention is a polymer compound which is removed by an organic solvent.

In the specification, the polymer compound removed by the term "organic solvent" is a natural or synthetic compound having a molecular weight of 5,000 or more, and denotes a compound having solubility to an organic solvent.

A polymer compound used in the present invention should be easily removed after metal-deposition and plating for manufacturing a hollow microneedle, and thus, the inventors has removed the polymer compound (which is a component of a metal-plated solid microstructure) by dissolving the polymer compound in an organic solvent.

The polymer compound used in the present invention is acrylonitrile styrene (AS), polyimide, polyethylene, polyester, polyacryl, polyacetylene, styrene, teflon, polyvinyl chloride, polyurethane, nylon, sulfonic resin, or epoxy polymer. For example, the polymer compound may be an epoxy polymer.

The organic solvent used in the present invention includes benzene, toluene, xylene, hexane, ester, acetone, alcohol, and amine, but is not limited thereto. All polar or nonpolar solvents, which are commonly used to dissolve a polymer compound, may be used. For example, when an epoxy polymer is used as the polymer compound, N-methyl pyrrolidine (NMP) may be used as a solvent.

Operation (b): Bringing the Solution of the Viscous Material into Contact with a Frame In the specification, after coating a viscous material (for example, a polymer compound) changed to a fluid, a lifting frame is brought into contact with an interface of the viscous material. According to an implementation example of the present invention, a diameter of the lifting frame may be changed, in which case the diameter of the lifting frame may be adjusted within a range from 1 μm to 1,000 μm or adjusted within a range from 10 μm to 500 μm.

The diameter of the lifting frame affects various appearance factors (i.e., an effective length, an internal diameter, an external diameter, sharpness, an aspect ratio, etc.) of a finally manufactured hollow microneedle, and particularly, acts as a variable that changes an effective length, diameter, and sharpness of a solid microstructure, namely, an effective length, sharpness, external diameter, and internal diameter of a hollow microstructure. As the diameter of the lifting frame increases, an external diameter and internal diameter of a hollow microneedle increase, an effective length increases, and sharpness decreases.

A frame used in the specification may be patterned. In this case, the pattern may be formed from a single array to a multi-array, and a pitch between frames may be 1 μm to 2,000 μm. As another example, the pitch between the frames may be 100 μm to 1,000 μm.

Operation (c): Lifting the Substrate, the Frame, or the Substrate and the Frame for the Contacted Frame and Substrate to be Spaced Apart from Each Other to Thereby Manufacture a Solid Microstructure The term "solid microstructure" used in the specification denotes a microstructure that is manufactured as one body without a hollow space and a mold of a hollow microneedle.

In the present invention, by lowering a temperature of a viscous material (for example, polymer material) changed to a fluid to approach the glass transition temperature, viscosity increases. In operation (c), the viscosity affects various appearance factors (i.e., an effective length, an internal diameter, an external diameter, sharpness, an aspect ratio, etc.) of a finally manufactured hollow microneedle, and particularly, acts as a variable that changes an effective length of a solid microstructure and an effective length of a hollow microstructure. In operation (c), as the viscosity of the viscous material increases, an effective length of a hollow microstructure increases.

According to an implementation example of the present invention, the temperature of the viscous material is adjusted within a range from a glass transition temperature to 120° C., thereby adjusting viscosity of the viscous material.

In the specification, the term "glass transition temperature" denotes a temperature at which a fluid material having viscosity is solidified. Therefore, it is impossible to perform a lifting process on a solidified material at a temperature lower than the glass transition temperature. When a temperature is too high, viscosity decreases, and thus, it is difficult to perform a lifting process. As a result, it is unable to manufacture a solid microstructure.

According to an implementation example of the present invention, the viscosity of the viscous material which is adjusted in operation (c) may be 50 Poise to 10,000 Poise, 80 Poise to 8,000 Poise, or 100 Poise to 6,500 Poise.

In the specification, the term "separation" denotes increasing a distance between contacted elements to broaden a gap between the contacted elements. The inventors have manufactured a solid microstructure by lifting (moving upward) a frame contacting a viscous material, but is not limited thereto. As another example, the solid microneedle may be manufactured by a method that downward moves a substrate to separate the substrate from a frame when the frame is fixed, and a method that upward and downward moves a frame and a substrate simultaneously to separate the substrate from the frame.

According to the present invention, by adjusting a lifting speed of a polymer having viscosity, various appearance factors (i.e., an effective length, an internal diameter, an external diameter, sharpness, an aspect ratio, etc.) of a finally manufactured hollow microneedle may be adjusted, and particularly, an effective length of a solid microstructure and an effective length of a hollow microneedle may be adjusted. As the lifting speed increases, the effective length of the hollow microneedle increases.

In the specification, the term "lifting speed" includes an upward or downward moving speed of a frame or a substrate and moreover a relative speed at which the frame and the substrate is spaced apart from each other when the frame and the substrate simultaneously move upward and downward.

The lifting speed used in the specification is 0.1 μm/s to 2,000 μm/s, and for example, may be 1 μm/s to 1,000 μm/s, A length of the final solid microstructure may be adjusted by a correlation (multiplication) between a lifting speed and a lifting time. For example, the multiplication of the lifting speed (μm/s) and lifting time (s) used in the present invention may be 500 μm to 10,000 μm, 500 μm to 5,000 μm, or 1,000 μm to 3,000 μm.

Operation (d): Depositing Metal on the Solid Microstructure

According to the present invention, metal is deposited on a manufactured solid microstructure, thus more facilitating a metal-plating reaction for manufacturing a hollow microneedle after the deposition.

In the specification, the term "deposition" denotes that a material to be coated is vaporized or sublimated for enhancing the mechanical intensity thereof in a physical method or a chemical method, and thus coagulated on a substrate surface in units of an atom or a molecule, thereby forming a film. As the deposition of the present invention, all physical vapor depositions and chemical vapor depositions which are commonly used in the art may be used.

According to an implementation example of the present invention, the metal for deposition of the present invention is stainless steel, Al, Cr, Ni, Au, Ag, Cu, Ti, Co, or an alloy thereof. For example, Ag may be chemical-vapor-deposited in Tollens reaction.

In the present invention, Ag which is precipitated through a reduction reaction using Tollens reagent "$Ag_2O+NH_4OH+H_2O$" is deposited on a solid microstructure. The Tollens reaction does not need a heating process, a pressurizing process, and a separate cooling process unlike physical vapor deposition using sputtering, and thus is more favorable to metal deposition on a target surface.

Operation (e) Protecting an Upper Portion of the Metal-Deposited Solid Microstructure and Metal-Plating a Surface of the Microstructure In the specification, by plating a solid microstructure, the base of a hollow microneedle may be provided. According to the present invention, various appearance factors (i.e., an internal diameter and hardness) of a finally manufactured hollow microneedle may be varied by adjusting a plating thickness. As the plating thickness increases, an external diameter and hardness of the hollow microneedle increase, an effective length increases. The plating thickness used in the present invention is 5 μm to 100 μm, and for example, may be 10 μm to 50 μm.

A plating material used in the present invention, for example, includes Ni, stainless steel, Al, Cr, cobalt-based alloy, Ti, or an alloy thereof, but is not limited thereto. The plating material is metal applicable to a body, and is metal that does not have toxicity, carcinogenicity, and rejection to a body, is good in mechanical properties such as tension intensity, elastic modulus, and wear resistance, and has anticorrosion for enduring a corrosive environment in a body. As the plating material, all metals known in the art may be used.

According to an implementation example of the present invention, the plating metal of the present invention is stainless steel, Al, Cr, Ni, Au, Ag, Cu, Ti, Co, or an alloy thereof. For example, the plating metal of the present invention is Ni.

Operation (f) Removing the Solid Microstructure to Obtain a Hollow Microstructure After the plating process, by removing the solid microneedle, a hollow microneedle may be manufactured. The solid microneedle may be removed by dissolving the solid microneedle in an appropriate organic solvent or by burning the solid microneedle, or may be removed physically. The solid microneedle is removed using the appropriate organic solvent.

To easily pass through skin, an antifriction such as glycerin may be coated on a metal microneedle. An anticoagulation solution such as citrate or EDTA may be coated on a hollow metal microneedle, for preventing blood coagulation in collecting blood.

According to an implementation example of the present invention, the method of the present invention may further include cutting the top of the hollow microneedle of the present invention through adjustment within a bevel angle of 0 degrees to 60 degrees.

In the specification, by providing the bevel angle of the top of the hollow microneedle, the internal diameter and sharpness of the hollow microneedle can increase. As a method of adjusting the bevel angle of the present invention, all precise cutting methods which are commonly used in the art may be used, and for example, a laser or a microsaw (dicing saw) may be used for cuffing. By adjusting the bevel angle, various cross-sectional areas of an internal diameter and sharpness suitable for use may be provided. The bevel angle is adjusted within a range from 0 degrees to 90 degrees, and for example, may be adjusted within a range from 0 degrees to 60 degrees.

According to an implementation example of the present invention, in the hollow microstructure, a relationship between an effective length, the lifting speed, a diameter of the lifting frame, and the coating thickness of the viscous material is expressed as Formula.

$$Y=6000/(x-b)^{1/2}$$ [Formula]

where Y denotes the effective length (μm) of the hollow microstructure, x denotes the internal diameter (μm) of the hollow microstructure, and b denotes "(diameter (μm) of lifting frame+coating thickness (μm) of viscous material)/50".

According to the present invention, a hollow microstructure having various appearances may be manufactured by adjusting an effective length, a lifting speed, a lifting frame, and a coating thickness, manufacturing temperature, coating thickness, and bevel angle cutting of a viscous material. The inventors have repeatedly performed an experiment in various conditions so as to build a manufacturing condition for forming a predictable appearance, and thus established a relationship between an effective length and internal diameter of a hollow microstructure, a diameter of a lifting frame, and a coating thickness of a viscous material. Accordingly, by simply adjusting a manufacturing condition for obtaining various effective lengths and/or internal diameters based on the purpose of production, the microstructure of the present invention may be manufactured to have a desired appearance. By using Formula, a microstructure having various appearances and uses may be manufactured depending on the necessary using the same production line. Accordingly, economical and efficient manufacturing may be enabled.

According to an implementation example of the present invention, the hollow microstructure of the present invention is a single-type hollow microneedle that is connected to a top of a hollow injector. In the specification, the term "hollow injector" denotes a hollow injector, having on bevel angle, which is commonly used to deliver drugs or collect a fluid sample in the art.

According to the present invention, by bringing the viscous material (coated on the substrate of the present invention) into contact with the distal end of the top of the hollow injector instead of the lifting frame, a hollow microneedle connected to the top of the hollow injector may be manufactured. When the hollow microneedle is manufactured by the method, an injector for delivering drugs and collecting a bio sample through transdermal administration may be produced simply and efficiently.

According to an implementation example of the present invention, the method of the present invention may further include obtaining a bent microneedle structure by sending wind in a specific direction before the solid microneedle which is formed in operation of lifting the contacted substrate and frame to be spaced apart from each other is hardened.

In the specification, the term "bending" denotes a ratio of a vertical distance from the top of the microneedle to the substrate surface disposed at the bottom of the microneedle and a distance in which the center of the microneedle maximally deviates from on a vertical line from the top to the bottom of the microneedle. A bending rate is 20:1 to 2:1, and for example, may be 10:1 to 2:1. According to the present invention, the bending rate and bending position of the microneedle may be variously varied by adjusting a winding speed, a winding time, a winding direction, and a winding position in the lifting operation. In the method of the present invention, the winding speed is 3 μm/s to 70 μm/s. For example, the winding speed may be 5 μm/s to 50 μm/s, or 7 μm/s to 20 μm/s.

In accordance with another aspect of the present invention, there is provided a hollow microneedle manufactured by the method used in the present invention.

One of advantages of the present invention is to enable the external appearance of the hollow microneedle to be variously varied so as to be suitable for each use. The sharpness, top diameter, bottom diameter, length, and aspect ratio of the solid microstructure may be adjusted through operations (a) to (d) of the method of the present invention for manufacturing the solid microstructure. Also, the method of the present invention may further include sending wind in a specific direction before the solid microstructure formed in the lifting operation is hardened, and thus, the bending rate and bending position of the hollow microneedle may be adjusted.

In the specification, the term "top" denotes one distal end of the microneedle having the minimum diameter, and the term "bottom" denotes an under distal end of the microneedle contacting the substrate.

In the specification, the term "effective length" denotes a vertical length from the top of the microneedle to the substrate surface disposed at the bottom of the microneedle. In the specification, the term "aspect ratio" denotes a ratio (height to diameter at base) of the maximum diameter of the microneedle to the vertical length from the top of the microneedle to the substrate surface disposed at the bottom of the microneedle.

In the specification, the term "sharpness" denotes a degree by which a diameter from the bottom to the top of the microneedle decreases. That is, as sharpness increases, a degree of decrease in the diameter is high.

According to an implementation example of the present invention, in the hollow microneedle, an effective length is 150 μm to 6,000 μm, an external diameter of an upper portion is 40 μm to 200 μm, an internal diameter of the top is 10 μm to 100 μm, an external diameter of a lower portion is 200 μm to 1,000 μm, an internal diameter of the bottom is 150 μm to 950 μm, a difference between the internal diameter and external diameter of the top and bottom is 10 μm to 50 μm, and an aspect ratio is 1:10 to 1:30. As another example, in the hollow microneedle, an effective length is 1,000 μm to 2,000 μm, an external diameter of an upper portion is 30 μm to 100 μm, an internal diameter of the top is 20 μm to 90 μm, an external diameter of a lower portion is 200 μm to 500 μm, an internal diameter of the bottom is 170 μm to 470 μm, a difference between the internal diameter and external diameter of the top and bottom is 20 μm to 30 μm, and an aspect ratio is 1:15 to 1:20. Especially, the aspect ratio may be 1:15 to 1:20.

The external diameter and internal diameter of the top, the internal diameter, thickness, length, sharpness, and aspect ratio of the bottom, the bending degree, and the bending position may be freely varied according to purposes.

According to an implementation example of the present invention, the hardness of the hollow microneedle of the present invention is 0.1 Newton (N) to 5 N.

In the specification, the term "hardness" denotes a force that resists to the change in a shape when an external force is applied to the solidified hollow microneedle. A hardness value enabling a microneedle to pass through skin is about 0.06 N. The hollow microneedle of the present invention has a hardness value far greater than 0.06 N, and thereby easily passes through all skins of a body, thus enabling the administration of drugs.

In accordance with another aspect of the present invention, there is provided a microvalve which includes: an internal microneedle, the internal microneedle being a hollow or solid microneedle; an external microneedle disposed at outside of the internal microneedle, spaced apart by a certain distance from a surface of the internal microneedle to surround the surface of the internal microneedle, and having the same surface curve as the internal microneedle, the external microneedle being a hollow microneedle; and a clipping device formed by bending a distal end of a lower portion of the external microneedle toward inside, bending a distal end of a lower portion of the internal microneedle toward outside, or respectively bending the distal ends of the respective bottoms of the external microneedle and internal microneedle toward the inside and the outside.

A space having a certain volume, which is disposed between the external microneedle and the internal microneedle, becomes a path through which a fluid flows. A microneedle, which acts as an internal valve by elasticity of the bent portion, moves according to the pressure intensity of a fluid to thereby obstruct or prevent the flow of the fluid, and thus acts as a fluid adjustment valve that adjusts a flow speed and a flow pressure.

In the specification, the term "valve" denotes a device that adjusts the flow or pressure of a fluid by blocking an open/close or partial path. According to the present invention, as described above in the implementation example, the sharpness, top diameter, bottom diameter, length, aspect ratio, bending rate, and bending position of the microstructure may be varied by adjusting the coating thickness, manufacturing temperature, lifting speed, lifting time, plating thickness, bevel angle, winding speed, and winding position of the viscous material. Therefore, two microneedles having the same surface curve are manufactured by accurately varying an external appearance, and, with the two microneedles as an internal microneedle and an external microneedle, an overlapped microneedle having a certain space between the internal microneedle and the external microneedle may be manufactured. The space between the microneedles becomes a path of a fluid, and the flow of the fluid is adjusted by a clipping device disposed at a distal end of a lower portion of each of the two microneedles.

In the specification, the term "microvalve" denotes a device that is disposed in a moving path of a fine fluid, and accurately adjusts a flow pressure and an amount of moved fluid by overall or partially blocking the flow of the fluid. According to the present invention, when the overlapped microneedle of the present invention is implanted into a film surrounding a fluid, the fluid inside the film may flow along the space of the overlapped microneedle, and the microvalve may accurately adjust the discharge of the fluid.

According to an implementation example of the present invention, the microvalve of the present invention is a glaucoma drainage device for treating glaucoma. In the specification, the term "glaucoma" denotes eye disease in which as an intraocular pressure becomes higher than a normal pressure (21 mmHg or more), the intraocular pressure presses an optic nerve to damage or destroy the optic nerve, and thus, sight is reduced or lost. The intraocular pressure is determined by equilibrium between production of tail water and a resistance to the outflow of the tail water. Generally, the rising of the intraocular pressure is caused by the increase in a resistance to the outflow of the tail water. Therefore, the smooth outflow of the tail water is important for treating glaucoma. According to the present invention, the overlapped microneedle of the present invention does hardly damage a film surface, and discharges a fluid surrounded by a film to the outside in a flow pressure and an amount that are accurately and finely adjusted. Accordingly, the overlapped microneedle of the present invention can be usefully used to treat glaucoma through the outflow of tail water.

In accordance with another aspect of the present invention, there is provided a biosensor which includes: (a) an internal microneedle, the internal microneedle being a hollow or solid microneedle; (b) an external microneedle disposed at outside of the internal microneedle, spaced apart by a certain distance from a surface of the internal microneedle to surround the surface of the internal microneedle, and having the same surface curve as the internal microneedle, the external microneedle being a hollow microneedle; (c) an insulator coated on an outer surface of the internal microneedle or an inner surface of the external microneedle; (d) a positive terminal connected to a distal end of the internal microneedle; a negative terminal connected to a distal end of the external microneedle; and (e) a measurement device for measuring a resistance, a current, or a voltage which is generated across the positive and negative terminals.

In the specification, the term "insulator" denotes a material that shows a resistance to the flow of a current, and thus has properties difficult to transfer electricity. According to the present invention, the insulator is disposed in the space between the internal microneedle and external microneedle of the overlapped microneedle of the present invention, and, after a distal end of an upper portion of the overlapped microneedle is implanted into a material to analyze, a voltage is applied to the positive terminal and negative terminal connected to a distal end of a lower portion of the overlapped microneedle. At this point, by measuring a generated voltage or resistance, the electrical characteristic of a material to measure may be detected.

According to an implementation example of the present invention, the biosensor of the present invention may further include a biomarker connected to a distal end of an upper portion of the internal microneedle and a distal end of an upper portion of the external microneedle.

In the specification, the term "biomarker" denotes a material that becomes an indicator for determining a biological condition of a living thing. According to the present invention, the biomarker is adhered between the distal ends of the overlapped microneedle of the present invention, and, after the biomarker is implanted into skin, by measuring a voltage generated across the two terminals, a biological condition of a living thing can be detected. For example, the biomarker of the present invention is a protein. In detail, when glucose oxidase (GOx) is used as the biomarker of the present invention, the overlapped microneedle with the glucose oxidase adhered thereto is implanted into skin of a target thing, and then, by measuring the change in a voltage, a glucose concentration in blood may be measured on the basis of the measured change in the voltage. Accordingly, the present invention performs a simple procedure that implants a simple device into a patient and performs measurement without blood collection and pain, thereby enabling the high-reliability measurement of blood sugar at low cost.

Advantageous Effects

The features and advantages of the present invention are as follows.

The present invention provides a method that manufactures a hollow microneedle having various external appearances by adjusting a coating thickness of a viscous material, a manufacturing temperature, a lifting speed, a lifting time, a plating thickness, and cutting of a bevel angle in a manufacturing process. Such a method has not been employed at all.

Moreover, in accordance with the present invention, a hollow microneedle having a desired external appearance may be simply and quickly manufactured at the low manufacturing cost.

Moreover, in accordance with the present invention, by manufacturing a hollow microneedle having characteristics of various external appearances, provided is a hollow microneedle that may deliver drugs and collect blood irrespective of species, races, individuals, regions of skin, and the viscosity and amount of the drugs.

Moreover, in accordance with the present invention, the hollow microneedle of the present invention may be manufactured in an array type, and manufactured as a single type microneedle that is coupled to a distal end of an injector compatible with a syringe.

Moreover, in accordance with the present invention, a microneedle in which the degree and position of bending may be adjusted is manufactured by the method of the present invention.

Moreover, in accordance with the present invention, by manufacturing a plurality of microneedles having the same surface curve in a method of adjusting an external appearance of the microneedle in accordance with the present invention, a microvalve and a biosensor having the microneedle type may be manufactured by a structure in which the microneedles overlap. The microvalve in which a flow pressure is finely adjusted in a simple structure and at low cost and the biosensor that reliably detects a target material from a body may be usefully used.

BRIEF DESCRIPTION OF DRAWING

FIGS. 7A to 7C are views schematically illustrating implementation examples of microneedles manufactured at a distal end of an injector.

FIGS. 8A to 8C are views schematically illustrating implementation examples of bent microneedles.

BEST MODE FOR THE INVENTION

Hereinafter, the present invention will be described in more detail through embodiments. The embodiments are merely for exemplifying the present invention, and it is obvious to those skilled in the art that the scope of the present invention is not limited by the embodiments according to the important point of the present invention.

Embodiment 1

Figure 1A:
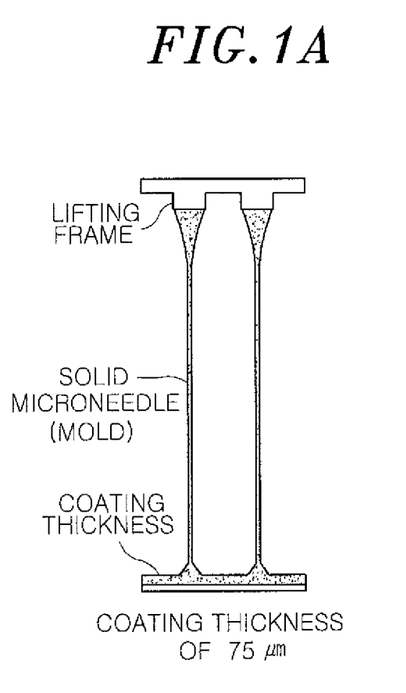
FIGS. 1A and 1B are views schematically illustrating detailed implementation examples of microneedles that are manufactured by adjusting a polymer coating thickness.
Figure 1B:
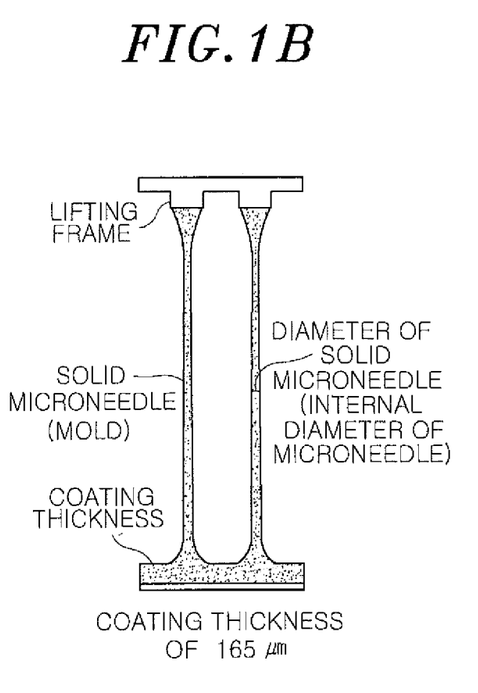

Varying an External Appearance of a Microneedle by Adjusting a Coating Thickness of a Polymer Solution A solid microstructure, i.e., a solid microneedle (a mold) is formed of an epoxy polymer "SU-8 2050 photoresist (microchem)" that is a polymer having viscosity of 14,000 cSt. SU-8 2050 is respectively coated on a metal or silicon substrate to a thickness of 75 µm and 165 µm and then maintained at a temperature of 120° C. for 5 minutes, thereby enabling the flux of SU-8 2050 to be maintained. Subsequently, the SU-8 2050 is contacted to a 3×3 patterned frame having a diameter of 200 µm While slowly lowering a temperature of the substrate to 70° C. to 60° C., the coated SU-8 2050 has viscosity enabling lifting. At this point, by lifting a lifting frame for 5 minutes at a speed of 10 µm/s, as illustrated in FIGS. 1A and 1B, an initial solid structure i.e., an initial solid microneedle (an initial mold) having a length of 3,000 µm is formed. By increasing a second lifting speed or cutting, the initial solid structure may be spaced apart from the lifting frame.

As a result, in an initial coating thickness of 75 µm, a solid microstructure is formed to have a diameter of 30 µm in upper portion thereof, a diameter of 200 µm in lower portion thereof, and a length of 1,500 µm, and chemical-vapor-deposited in Tollens reaction. In an initial coating thickness of 165 µm, a solid microstructure is formed to have a diameter of 40 µm upper portion thereof, a diameter of 300 µm in lower portion thereof, and a length of 2,000 µm, and chemical-vapor-deposited in Tollens reaction. Subsequently, the top of each of the solid microneedles is protected with enamel or SU-8 2050. Processing the enamel or the SU-8 2050 on the top prevents the top from being plated in a subsequent process. The solid microstructure is overall plated with metal and then cut by a laser and a microsaw, thereby forming a hollow microstructure.

Subsequently, a surface of the solid microneedle whose the top has been protected is electroplated with nickel (Ni). The Ni electroplating is performed by 0.206 µm/min per 1 A/dm2 for 75 minutes so that a thickness of the electroplated Ni may become 20 µm. The electroplated structure is put into an SU-8 remover (microchem) of 60° C. to 100° C. for one hour to remove the solid microstructure of SU-8 2050 and sealed enamel, thereby obtaining a hollow microneedle. In the obtained hollow microneedle, a hollow microneedle is manufactured to have an external diameter of 70 µm of an upper portion, an internal diameter of 30 µm in the upper portion thereof, a diameter of 200 µm of a lower portion, and a length of 1,500 µm from the initial coating thickness of 75 µm, and a hollow microneedle is manufactured to have an external diameter of 100 μm of an upper portion, an internal diameter of 60 μm of the top, a diameter of 300 μm of a lower portion, and a length of 2,000 μm from the initial coating thickness of 165 μm. The hardness of the manufactured hollow microneedle indicates a value of 1-2N, which is a value far greater than 0.06 N that is a hardness value enabling the hollow microneedle to pass through skin.

Embodiment 2

Varying an External Appearance of a Microneedle by Adjusting a Diameter of a Lifting Frame A solid microstructure is formed of an epoxy polymer "SU-8 2050 photoresist" that is a polymer having viscosity of 14,000 cSt. SU-8 2050 is coated on a metal or silicon substrate to a thickness of 75 μm, and then maintained at a temperature of 120° C. for 5 minutes, thereby enabling the flux of the SU-8 2050 to be maintained. Subsequently, the SU-8 2050 is contacted to a 3×3 patterned frame having a diameter of 200 μm and a 3×3 patterned frame having a diameter of 500 μm, respectively. While slowly lowering a temperature of the substrate to 70° C. to 60° C., the coated SU-8 2050 has viscosity enabling lifting.

Figure 2A:
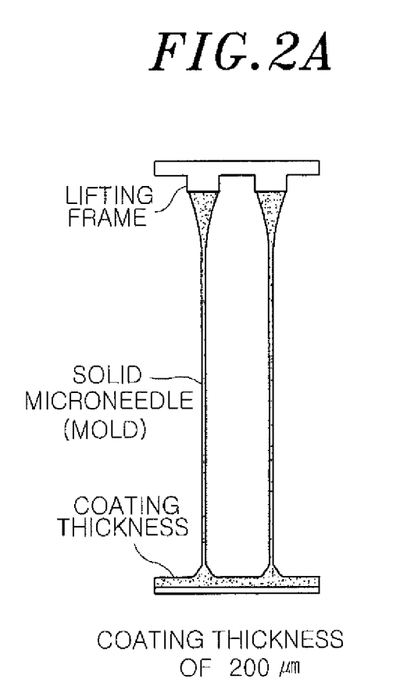
FIGS. 2A and 2B are views schematically illustrating detailed implementation examples of microneedles that are manufactured by adjusting a diameter of a lifting frame.
Figure 2B:
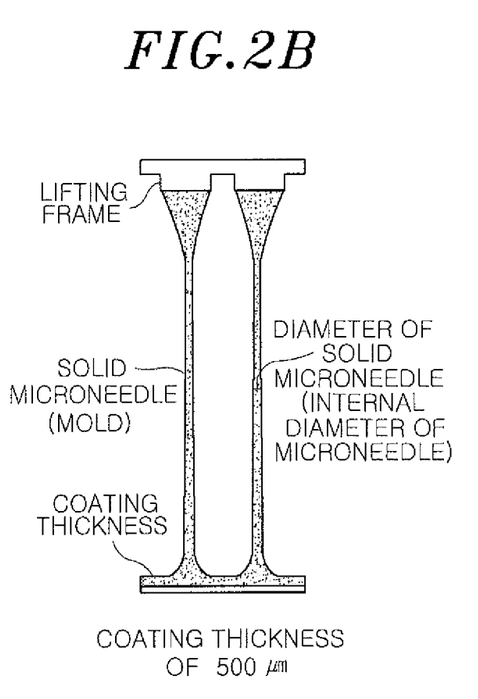

At this point, by lifting a lifting frame for 5 minutes at a speed of 10 μm/s, as illustrated in FIGS. 2A and 2B, an initial solid structure having a length of 3,000 μm is formed. By increasing a second lifting speed or cutting, the initial solid structure is spaced apart from the lifting frame. As a result, by a lifting frame having an initial diameter of 200 μm, a solid microstructure is formed to have a diameter of 30 μm in an upper portion thereof, a diameter of 200 μm of a lower portion thereof, and a length of 1,500 μm, and chemical-vapor-deposited in Tollens reaction. By a lifting frame having an initial diameter of 500 μm, a solid microstructure is formed to have a diameter of 40 μm of an upper portion, a diameter of 500 μm of a lower portion, and a length of 2,000 μm, and chemical-vapor-deposited in Tollens reaction. Subsequently, the top of each of the solid microneedles is protected with enamel or SU-8 2050. The reason that processes enamel or SU-8 2050 on the top is the same as the embodiment 1.

Subsequently, a surface of the solid microneedle whose the top has been protected is electroplated with Ni. The Ni electroplating is performed by 0.206 μm/min per 1 A/dm2 for 75 minutes so that a thickness of the electroplated Ni may become 20 μm. The electroplated structure is put into an SU-8 remover of 60° C. to 100° C. for one hour to remove the solid microneedle of SU-8 2050 and sealed enamel, thereby obtaining a hollow microneedle. In the obtained hollow microneedle, a hollow microneedle is manufactured to have an external diameter of 70 μm in an upper portion thereof, an internal diameter of 30 μm in the upper portion, a diameter of 200 μm of a lower portion thereof, and a length of 1,500 μm from the lifting frame having an initial diameter of 200 μm, and a hollow microneedle is manufactured to have an external diameter of 100 μm in an upper portion thereof, an internal diameter of 60 μm in the upper portion thereof, a diameter of 500 μm in a lower portion thereof, and a length of 2,000 μm from the lifting frame having an initial diameter of 500 μm. The hardness of the manufactured hollow microneedle indicates a value of 1-2N, which is a value far greater than 0.06 N that is a hardness value enabling the hollow microneedle to pass through skin.

Embodiment 3

Varying an External Appearance of a Microneedle by Adjusting a Temperature

Figure 3A:
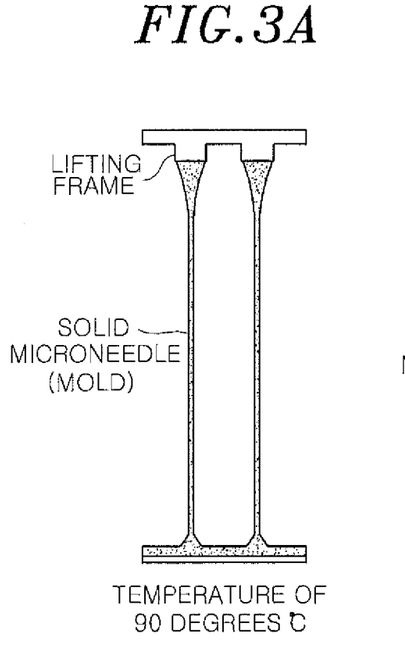
FIGS. 3A and 3B are views schematically illustrating detailed implementation examples of microneedles that are manufactured by adjusting a temperature of a polymer.
Figure 3B:
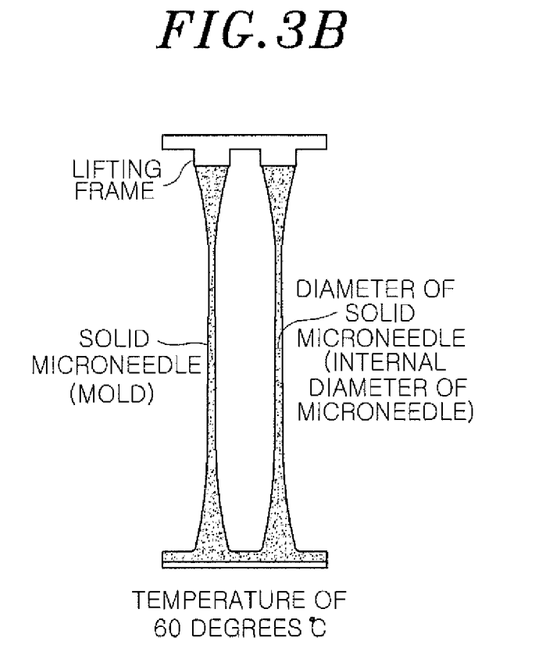

A solid microstructure is formed of an epoxy polymer "SU-8 2050 photoresist" that is a polymer having viscosity of 14,000 cSt. SU-8 2050 is coated on a metal or silicon substrate to a thickness of 75 μm, and then maintained at a temperature of 120° C. for 5 minutes, thereby enabling the flux of the SU-8 2050 to be maintained. Subsequently, the SU-8 2050 is contacted to a 3×3 patterned frame having a diameter of 200 μm. While slowly lowering a temperature of the substrate to 90° C. (adhesive strength of polymer: 1N, viscosity: 100 Poise) and 60° C. (adhesive strength of polymer: 2N, viscosity: 6,500 Poise), by lifting a lifting frame for 5 minutes at a speed of 10 μm/s, as illustrated in FIGS. 3A and 3B, an initial solid structure having a length of 3,000 μm is formed. By increasing a second lifting speed or cutting, the initial solid structure is spaced apart from the lifting frame. As a result, at an initial lifting temperature of 90° C., the solid microstructure is formed to have a diameter of 30 μm in an upper portion thereof, a diameter of 200 μm of a lower portion, and a length of 1,000 μm, and chemical-vapor-deposited in Tollens reaction. At an initial lifting temperature of 60° C., the solid microstructure is formed to have a diameter of 30 μm in an upper portion thereof, a diameter of 200 μm of a lower portion, and a length of 1,500 μm, and chemical-vapor-deposited in Tollens reaction. Subsequently, the upper portion of each of the solid microneedles is protected with enamel or SU-8 2050. The reason that processes the enamel or SU-8 2050 on the upper portion of the solid microneedles is the same as the embodiment 1. Subsequently, a surface of the solid microneedle whose the upper portion has been protected is electroplated with Ni. The Ni electroplating is performed by 0.206 μm/min per 1 A/dm2 for 75 minutes so that a thickness of the electroplated Ni may become 20 μm. The electroplated structure is put into an SU-8 remover of 60° C. to 100° C. for one hour to remove the solid microstructure of the SU-8 2050 and sealed enamel, thereby obtaining a hollow microneedle. In the obtained hollow microneedle, a hollow microneedle is manufactured to have an external diameter of 70 μm in an upper portion thereof, an internal diameter of 30 μm of the upper portion thereof, a diameter of 200 μm of a lower portion thereof, and a length of 1,000 μm at the initial lifting temperature of 90° C., and a hollow microneedle is manufactured to have an external diameter of 70 μm in an upper portion thereof, an internal diameter of 30 μmin the upper portion thereof, a diameter of 200 μm in a lower portion thereof, and a length of 1,500 μm at the initial lifting temperature of 60° C. The hardness of the manufactured hollow microneedle indicates a value of 1-2N, which is a value far greater than 0.06 N that is a hardness value enabling the hollow microneedle to pass through skin.

Embodiment 4

Figure 4A:
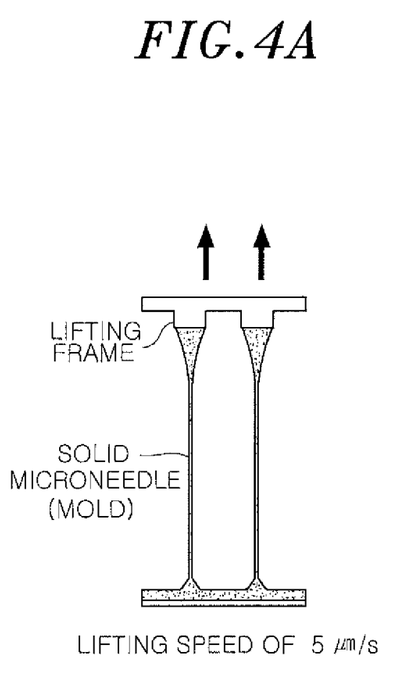
FIGS. 4A and 4B are views schematically illustrating detailed implementation examples of microneedles that are manufactured by adjusting a lifting speed.
Figure 4B:
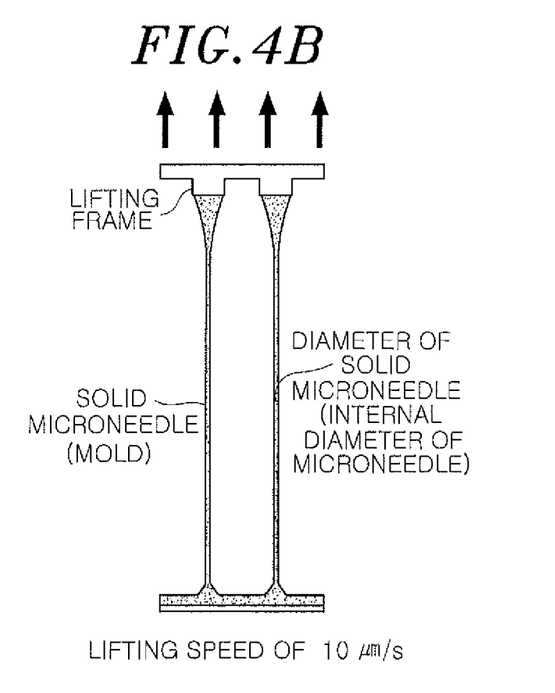

Varying an External Appearance of a Microneedle by Adjusting a Lifting Speed A solid microstructure is formed of an epoxy polymer "SU-8 2050 photoresist" that is a polymer having viscosity of 14,000 cSt. The SU-8 2050 is coated on a metal or silicon substrate to a thickness of 75 μm, and then maintained at a temperature of 120° C. for 5 minutes, thereby enabling the flux of SU-8 2050 to be maintained. Subsequently, the SU-8 2050 is contacted to a 3×3 patterned frame having a diameter of 200 μm. While slowly lowering a temperature of the substrate to 70° C. to 60° C., by respectively lifting a lifting frame for 5 minutes at a speed of 5 μm/s and a speed of 10 μm, as illustrated in FIGS. 4A and 4B, an initial solid structure having a length of 1,500 μm and an initial solid structure having a length of 3,000 μm are formed. By increasing a second lifting speed or cutting, each of the initial solid structures is spaced apart from the lifting frame. As a result, in a case of the speed of 5 μm/s, a solid microstructure is formed to have a diameter of 30 μm in an upper portion thereof, a diameter of 200 μm of a lower portion, and a length of 8.00 μm, and chemical-vapor-deposited in Tollens reaction. In a case of the speed of 10 μm/s, a solid microstructure is formed to have a diameter of 30 μm in an upper portion thereof, a diameter of 200 μm of a lower portion, and a length of 1,500 μm, and chemical-vapor-deposited in Tollens reaction. Subsequently, the upper portion of each of the solid microneedles is protected with enamel or SU-8 2050. The reason that processes the enamel or SU-8 2050 on the upper portion of the solid microneedle is the same as the embodiment 1.

Subsequently, a surface of the solid microneedle whose the upper portion has been protected is electroplated with Ni. The Ni electroplating is performed by 0.206 μm/min per 1 A/dm2 for 75 minutes so that a thickness of the electroplated Ni may become 20 μm. The electroplated structure is put into an SU-8 remover of 60° C. to 100° C. for one hour to remove the solid microstructure of SU-8 2050 and sealed enamel, thereby obtaining a hollow microneedle. In the obtained hollow microneedle, a hollow microneedle is manufactured to have an external diameter of 70 μm in an upper portion thereof, an internal diameter of 30 μm of the upper portion thereof, a diameter of 200 μm in a lower portion thereof, and a length of 800 μm at the speed of 5 μm/s, and a hollow microneedle is manufactured to have an external diameter of 70 μm in an upper portion thereof, an internal diameter of 30 μm of the upper portion thereof, a diameter of 200 μm of a lower portion thereof, and a length of 1,500 μm at the speed of 10 μm/s. The hardness of the manufactured hollow microneedle indicates a value of 1-2N, which is a value far greater than 0.06 N that is a hardness value enabling the hollow microneedle to pass through skin.

The embodiment in which an external appearance of a microneedle is varied by adjusting the lifting speed has been described above, but an external appearance of a microneedle may also be varied by adjusting the lifting time. Therefore, an external appearance of the final solid microstructure may be adjusted with a correlation (multiplication) between the lifting speed and the lifting time.

The inventors fix a lifting speed, a lifting time, and a temperature by using SU-8 2050 photoresist having viscosity of 14,000 cSt, and thus have established a relationship between a diameter (μm) of a lifting frame, a coating thickness (μm) of a viscous material, and an effective length (μm) and internal diameter (μm) of a hollow microstructure. That is, the SU-8 2050 is coated on a metal or silicon substrate to various thicknesses, and then maintained at a temperature of 120° C. for 5 minutes, thereby enabling the flux of the SU-8 2050 to be maintained. Subsequently, the SU-8 2050 contacts a lifting frame having various diameters. While slowly lowering a temperature of the substrate to 90° C. (adhesive strength of polymer: 1N, viscosity: 100 Poise) and 60° C. (adhesive strength of polymer: 2N, viscosity: 6,500 Poise), by lifting a lifting frame for 5 minutes at a speed of 10 μm/s, a solid structure is formed. Subsequently, an operation of forming the hollow microstructure is as described above. Through such operations, a hollow microstructure having an external appearance shown in the following Table 1 is obtained.

TABLE 1

An effective length (μm) and internal diameter (μm) of a hollow microstructure according to a diameter (μm) of a lifting frame and a coating thickness (μm) of a viscous material

| | Effective length (μm) | Internal diameter (μm) | Diameter (μm) of lifting frame | Coating thickness (μm) of viscous material |
|---|---|---|---|---|
| 1 | 4800 | 15 | 200 | 470 |
| 2 | 4500 | 16 | 200 | 500 |
| 3 | 4200 | 19 | 500 | 350 |
| 4 | 3900 | 21 | 500 | 430 |
| 5 | 3600 | 22 | 500 | 460 |
| 6 | 3300 | 24 | 700 | 340 |
| 7 | 3000 | 26 | 700 | 400 |
| 8 | 2700 | 27 | 700 | 400 |
| 9 | 2400 | 29 | 700 | 510 |
| 10 | 2100 | 32 | 700 | 490 |
| 11 | 1800 | 37 | 800 | 500 |
| 12 | 1500 | 45 | 900 | 550 |
| 13 | 1200 | 66 | 1500 | 550 |
| 14 | 900 | 98 | 2000 | 700 |
| 15 | 600 | 200 | 3000 | 1850 |

On the basis of the result of Table 1, it has been established that a relationship between the diameter (μm) of the lifting frame, the coating thickness (μm) of the viscous material, the effective length (μm) of the hollow microstructure, and internal diameter (μm) of the hollow microstructure is expressed as the following Formula 1.

$$Y = 6000/(x-b)^{1/2} \qquad \text{[Formula 1]}$$

where Y denotes the effective length (μm) of the hollow microstructure, x denotes the internal diameter (μm) of the hollow microstructure, and b denotes "(diameter (μm) of lifting frame+coating thickness (μm) of viscous material)/50".

Embodiment 5

Figure 5A:
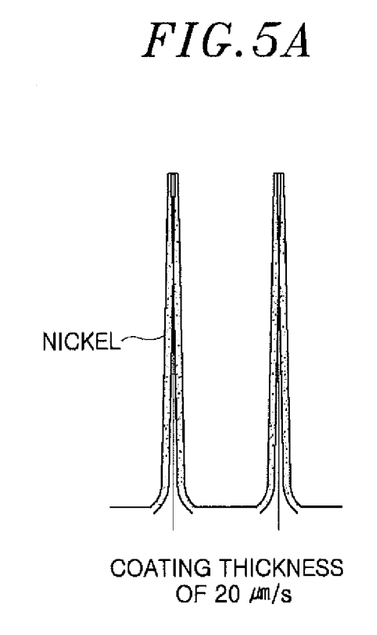
FIGS. 5A and 5B are views schematically illustrating detailed implementation examples of microneedles that are manufactured by adjusting a plating thickness.
Figure 5B:
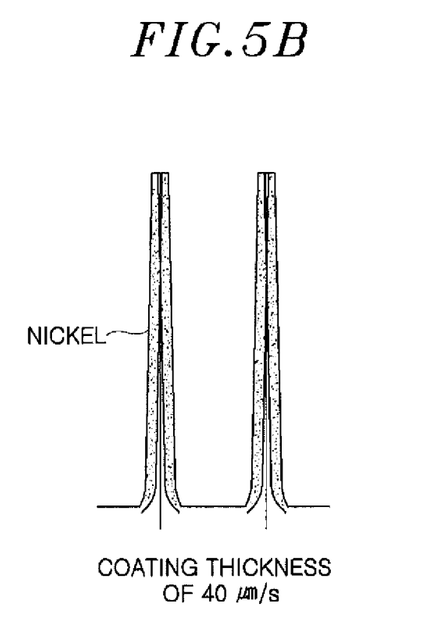

Varying an External Appearance of a Microneedle by Adjusting a Coating Thickness A solid microstructure is formed of an epoxy polymer "SU-8 2050 photoresist" that is a polymer having viscosity of 14,000 cSt. The SU-8 2050 is coated on a metal or silicon substrate to a thickness of 75 μm, and then maintained at a temperature of 120° C. for 5 minutes, thereby enabling the flux of the SU-8 2050 to be maintained. Subsequently, the SU-8 2050 is contacted to a 3×3 patterned frame having a diameter of 200 μm. While slowly lowering a temperature of the substrate to 70° C. to 60° C., by lifting a lifting frame for 5 minutes at a speed of 10 μm, an initial solid structure having a length of 3,000 μm is formed. By increasing a second lifting speed or cutting, the initial solid structure is spaced apart from the lifting frame. As a result, a solid microstructure is formed to have a diameter of 30 μm in an upper portion thereof, a diameter of 200 μm of a lower portion thereof, and a length of 1,500 μm, and chemical-vapor-deposited in Tollens reaction. Subsequently, the upper portion of the solid microneedle is protected with enamel or SU-8 2050. The reason that processes the enamel or SU-8 2050 on the upper portion of the solid microneedle is the same as the embodiment 1. Then, a surface of the solid microneedle whose the upper portion has been protected is electroplated with Ni. The Ni electroplating is performed by 0.206 μm/min per 1 A/dm2 for 75 minutes so that respective thicknesses of the electroplated Ni may become 20 μm and 40 μm (see FIGS. 5A and 5B). The electroplated structure is put into an SU-8 remover of 60° C.

to 100° C. for one hour to remove the solid microstructure of the SU-8 2050 and sealed enamel, thereby obtaining a hollow microneedle. In the obtained hollow microneedle, a hollow microneedle is manufactured to have an external diameter of 70 μm in an upper portion thereof, an internal diameter of 30 μm of the upper portion thereof, a diameter of 200 μm of a lower portion thereof, and a length of 1,500 μm from the metal thickness of 20 μm, and a hollow microneedle is manufactured to have an external diameter of 110 μm in an upper portion thereof, an internal diameter of 30 μm of the upper portion thereof, a diameter of 200 μm of a lower portion thereof, and a length of 1,500 μm from the metal thickness of 40 μm. The hardness of the manufactured hollow microneedle indicates a value of 1-2N, which is a value far greater than 0.06 N that is a hardness value enabling the hollow microneedle to pass through skin.

Embodiment 6

Figure 6A:
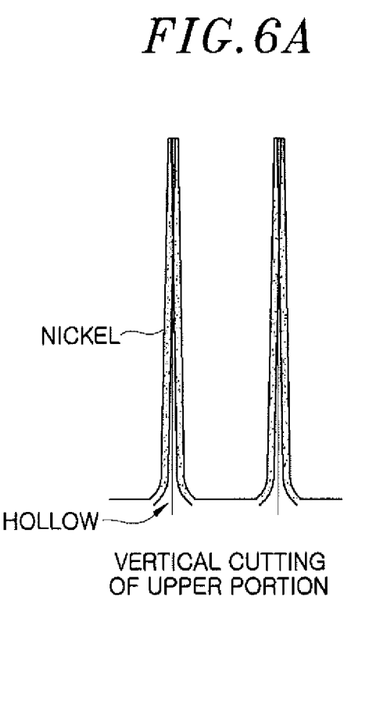
FIGS. 6A and 6B are views schematically illustrating detailed implementation examples of microneedles that are manufactured by adjusting a bevel angle of an upper portion.
Figure 6B:
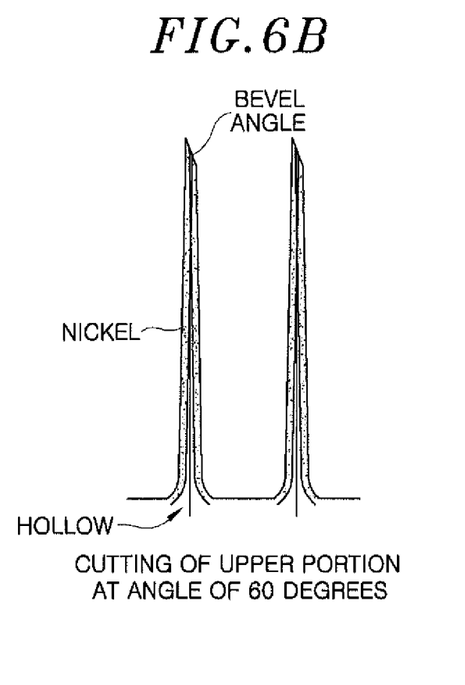

Varying an External Appearance of a Microneedle by Adjusting Cutting of a Bevel Angle A solid microstructure is formed of an epoxy polymer "SU-8 2050 photoresist" that is a polymer having viscosity of 14,000 cSt. The SU-8 2050 is coated on a metal or silicon substrate to a thickness of 75 μm, and then maintained at a temperature of 120° C. for 5 minutes, thereby enabling the flux of the SU-8 2050 to be maintained. Subsequently, the SU-8 2050 is contacted to a 3×3 patterned frame having a diameter of 200 μm. While slowly lowering a temperature of the substrate to 70° C. to 60° C., by lifting a lifting frame for 5 minutes at a speed of 10 μm, an initial solid structure having a length of 3,000 μm is formed. By increasing a second lifting speed or cutting, the initial solid structure is spaced apart from the lifting frame. As a result, a solid microstructure is formed to have a diameter of 30 μm in an upper portion, a diameter of 200 μm of a lower portion, and a length of 1,500 μm, and chemical-vapor-deposited in Tollens reaction. Subsequently, the upper portion of the solid microneedle is protected with enamel or SU-8 2050. The reason that processes the enamel or SU-8 2050 on the upper portion of the solid microneedle is the same as the embodiment 1. Then, a surface of the solid microneedle whose the upper portion has been protected is electroplated with Ni. The Ni electroplating is performed by 0.206 μm/min per 1 A/dm2 for 75 minutes and 200 minutes so that thicknesses of the electroplated Ni may become 20 μm. Subsequently, the upper portions of the electroplated solid microstructure are respectively cut at a vertical angle (angle of 0 degrees), an angle of 45 degrees, and an angle of 60 degrees by a laser. Then, each of the structures is put into an SU-8 remover of 60° C. to 100° C. for one hour to remove the solid microstructure of the SU-8 2050 and sealed enamel, thereby obtaining hollow microneedles illustrated in FIGS. 6A and 6B. FIG. 6A illustrates an example of a hollow microneedle that has been obtained by vertically cutting an upper portion of a microstructure, and FIG. 6B illustrates an example of a hollow microneedle that has been finished by cutting an upper portion of a microstructure at a specific angle (for example, 60 degrees). In the obtained hollow microneedles, a hollow microneedle is manufactured to have an external diameter of 70 μm in an upper portion, an internal diameter of 30 μm of the top, a diameter of 200 μm of a lower portion, and a length of 1,500 μm. In this case, an area of the internal diameter increases by 1.4 times a case in which the upper portion is cut at an angle of 45 degrees, and increases by 2 times a case in which the upper portion is cut at an angle of 60 degrees. Also, sharpness increases according to a cut bevel angle. The hardness of the manufactured hollow microneedle indicates a value of 1-2N, which is a value far greater than 0.06 N that is a hardness value enabling the hollow microneedle to pass through skin.

Embodiment 7

Manufacturing a Single Microneedle Contacting a Hollow Injector Structure

A solid microstructure contacting a distal end of a single hollow injector is formed of an epoxy polymer "SU-8 2050 photoresist" that is a polymer having viscosity of 14,000 cSt. The SU-8 2050 is respectively coated on a metal or silicon substrate to a thickness of 165 μm, and then maintained at a temperature of 120° C. for 5 minutes, thereby enabling the flux of the SU-8 2050 to be maintained. Subsequently, the SU-8 2050 is contacted to a distal end of a 23-gauge hollow injector having a diameter of 400 μm. While slowly lowering a temperature of the substrate to 70° C. to 60° C., the coated SU-8 2050 has viscosity enabling lifting. At this point, by lifting a lifting frame for 13 minutes at a speed of 10 μm/s, an initial solid structure having a length of 7,800 μm is formed. By increasing a second lifting speed or cutting, the initial solid structure may be spaced apart from the lifting frame. As a result, in an initial coating thickness of 75 μm a solid microstructure is formed to have a diameter of 30 μm in an upper portion thereof, a diameter of 400 μm of a lower portion thereof, and a length of 4,000 μm at a distal end of a hollow injector, and chemical-vapor-deposited in Tollens reaction. Subsequently, the upper portion of the single solid microneedle is protected with enamel or SU-8 2050. Processing the enamel or SU-8 2050 on the upper portion of the single solid microneedle prevents the upper portion from being plated in a subsequent process. The single solid microstructure is overall plated with metal and then cut by a laser and a microsaw, thereby forming a hollow microstructure. Subsequently, a surface of the solid microneedle whose the upper portion has been protected is electroplated with Ni. The Ni electroplating is performed by 0.206 μm/min per 1 A/dm2 for 75 minutes a thickness of the electroplated Ni may become 120 μm. Subsequently, the upper portions of the plated solid microstructures are respectively cut at a vertical angle and an angle of 45 degrees. Then, each of the structures is put into an SU-8 remover of 60° C. to 100° C. for one hour to remove the solid microstructure of the SU-8 2050, thereby obtaining a hollow microneedle contacting a hollow injector. The obtained hollow microneedle has an external diameter of 70 μm in an upper portion thereof, an internal diameter of 30 μm of the upper portion thereof, a diameter of 400 μm of a lower portion thereof, and a length of 4,000 μm. The hardness of the manufactured hollow microneedle indicates a value of 1-2N, which is a value far greater than 0.06 N that is a hardness value enabling the hollow microneedle to pass through skin.

Figure 7A:
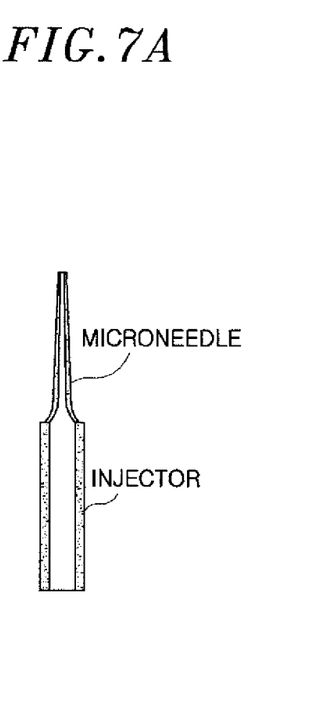
FIG. 7A is a view schematically illustrating a detailed implementation example of a short microneedle manufactured at the distal end of the injector.
Figure 7B:
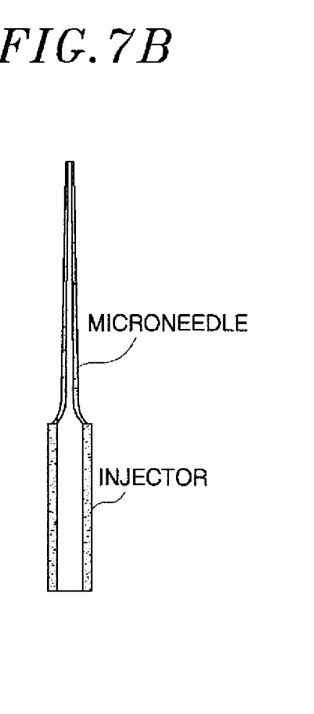
FIG. 7B is a view schematically illustrating a detailed implementation example of a long microneedle manufactured at a distal end of an injector.
Figure 7C:
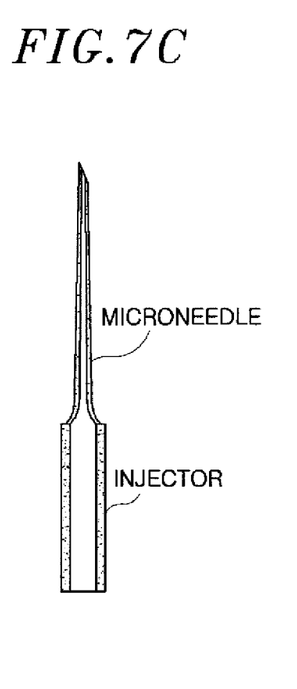
FIG. 7C is a view schematically illustrating a detailed implementation example of a microneedle, having a bevel angle, manufactured at a distal end of an injector.

FIGS. 7A to 7C are diagrams illustrating variously implemented examples of microneedles provided at a distal end of an injector. FIG. 7A illustrates a short microneedle manufactured at the distal end of the injector, FIG. 7B illustrates a long microneedle manufactured at a distal end of an injector, and FIG. 7C illustrates a microneedle, having a bevel angle formed at the distal end of the injector, manufactured by the above-described method.

Embodiment 8

Manufacturing a Bent Microneedle Contacting a Hollow Injector Structure

A solid microstructure contacting a distal end of a single hollow injector is formed of an epoxy polymer "SU-8 2050 photoresist (microchem)" that is a polymer having viscosity of 14,000 cSt. The SU-8 2050 is respectively coated on a metal or silicon substrate to a thickness of 165 µm, and then maintained at a temperature of 120° C. for 5 minutes, thereby enabling the flux of the SU-8 2050 to be maintained. Subsequently, the SU-8 2050 is contacted to a distal end of a 23-gauge hollow injector having a diameter of 400 µm. While slowly lowering a temperature of the substrate to 70° C. to 60° C., the coated SU-8 2050 has viscosity enabling lifting. At this point, by lifting a lifting frame for 13 minutes at a speed of 10 µm/s, an initial solid structure having a length of 7,800 µm is formed. Before the formed initial solid structure is hardened, by processing the initial solid structure in the wind of 10 µm/s in a specific direction, a bent solid structure whose a lower portion is spaced apart by a distance of 500 µm from a distal end of a contacted injector is manufactured. As the same bent effect, the lower portion of the solid structure from the distal end of the contacted injector is spaced apart by a distance of 500 µm, and an initial solid structure is bent.

Figure 8A:
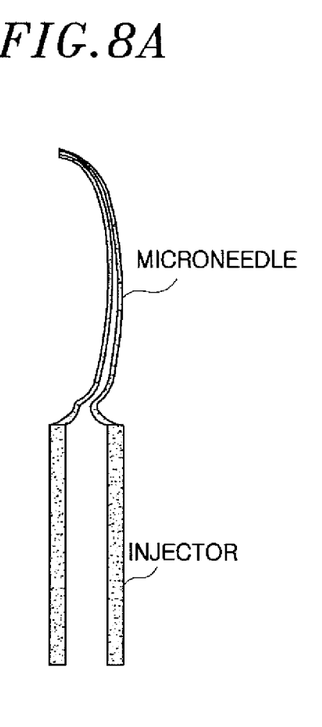
FIG. 8A is a view schematically illustrating a detailed implementation example of a microneedle bent from a distal end of an injector.
Figure 8B:
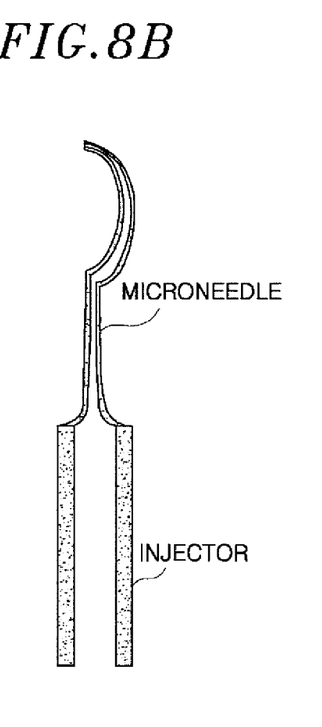
FIG. 8B is a view schematically illustrating a detailed implementation example of a microneedle bent from a central position of a microneedle structure.
Figure 8C:
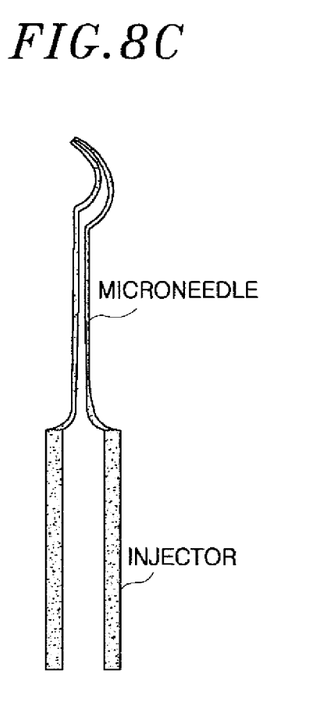
FIG. 8C is a view schematically illustrating a detailed implementation example of a microneedle bent at a distal end of a microneedle structure.

By increasing a second lifting speed or cutting, the bent solid structure may be spaced apart from the lifting frame. As a result, a single solid microstructure whose an upper portion and a lower portion are vertically spaced apart from each other by a distance of 500 µm and which is bent at respective portions corresponding to a diameter of 30 µm in the upper portion, a diameter of 200 µm in the lower portion, a length of 3,000 µm, and a length of 1,500 µm is obtained at a distal end of a hollow injector, and chemical-vapor-deposited in Tollens reaction. Subsequently, the upper portion of the single solid microstructure is protected with enamel or SU-8 2050. Processing the enamel or SU-8 2050 on the upper portion prevents the upper portion from being plated in a subsequent process. The single solid microstructure is overall plated with metal and then cut by a laser and a microsaw, thereby forming a hollow microstructure. Subsequently, a surface of the solid microneedle whose the upper portion has been protected is electroplated with Ni. The Ni electroplating is performed by 0.206 µm/min per 1 A/dm2 for 75 minutes so that a thickness of the electroplated Ni may become 20 µm. Subsequently, the upper portions of the plated solid microstructures are respectively cut at a vertical angle and an angle of 45 degrees. Then, each of the structures is put into an SU-8 remover of 60° C. to 100° C. for one hour to remove the solid microstructure of the SU-8 2050, thereby obtaining a hollow microneedle contacting a hollow injector. The upper portion and lower portion of the single solid microstructure are vertically spaced apart from each other by a distance of 500 µm, and the single solid microstructure is bent at respective portions corresponding to a diameter of 30 µm of the upper portion, a diameter of 200 µm of the lower portion, a length of 3,000 µm, and a length of 1,500 µm. The hardness of the manufactured hollow microneedle indicates a value of 1-2N, which is a value far greater than 0.06 N that is a hardness value enabling the hollow microneedle to pass through skin. FIGS. 8A to 8C are diagrams schematically illustrating implementation examples of bent microneedles. FIG. 8A illustrates a microneedle bent from a distal end of an injector, FIG. 8B illustrates a microneedle that is manufactured by the above-described method and bent from a central position of a microneedle structure, and FIG. 8C illustrates a microneedle bent at a distal end of the microneedle structure.

Embodiment 9

Manufacturing a Microvalve Using an Overlapped Microneedle Structure

Figure 9:
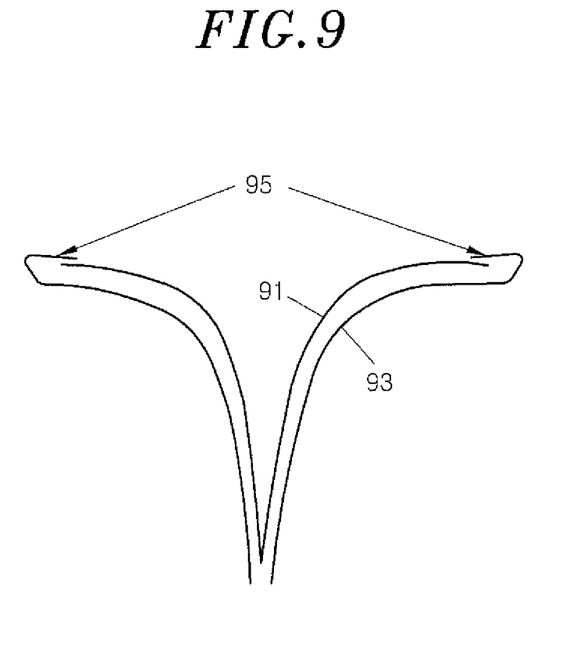
FIG. 9 is a schematic view illustrating a microvalve using an overlapped microneedle structure.

FIG. 9 is a schematic diagram illustrating a microvalve using an overlapped microneedle structure. A microvalve in accordance with an embodiment of the present invention includes: an internal microneedle 91 that is a hollow or solid microneedle; an external hollow microneedle 93 that is disposed at the outside of the internal microneedle 91, has the same surface curve as that of the internal microneedle 91, is spaced apart by a certain distance from a surface of the internal microneedle 91, and surrounds the surface of the internal microneedle 91; and a clipping device 95 that is formed by bending a distal end of a lower portion of the external microneedle 93 toward the inside thereof. A distal end of a lower portion of the internal microneedle 91 may be bent toward the outside, or the distal ends of the respective bottoms of the external microneedle 93 and internal microneedle 91 may be respectively bent toward the inside and the outside, thereby forming the clipping device 95. To manufacture the microvalve, as described above in the embodiments 1 to 6, a constant manufacturing condition is first fixed, and two hollow microstructures having the same external appearance are manufactured. Subsequently, one of the two manufactured microneedles is an external microneedle, and the other is inserted into the external microneedle and is an internal microneedle, thereby establishing an overlapped microneedle structure in which a constant internal interval of 5 µm to 10 µm is maintained between the two microneedles. Then, a distal end of a lower portion of the internal microneedle is fixed by bending a distal end of a lower portion of the external microneedle toward the distal end of the bottom of the internal microneedle, and thus, the internal microneedle becomes an internal valve adjustment device, thereby enabling a fluid to flow into a portion which is not covered by the bent portion.

A space having a certain volume, which is disposed between the external microneedle and the internal microneedle, becomes a path through which a fluid flows. The bent portion moves by elasticity according to the pressure intensity of a fluid to thereby obstruct or prevent the flow of the fluid, and thus serves as a fluid adjustment valve that adjusts a flow speed and a flow pressure. Therefore, for example, when the microvalve is used as a glaucoma drainage device for treating glaucoma caused by a high intraocular pressure, the microvalve can simplify glaucoma surgery and increase a treatment effect compared to the existing glaucoma drainage devices.

Embodiment 10

Manufacturing a Biosensor Using an Overlapped Microneedle Structure

Figure 10:
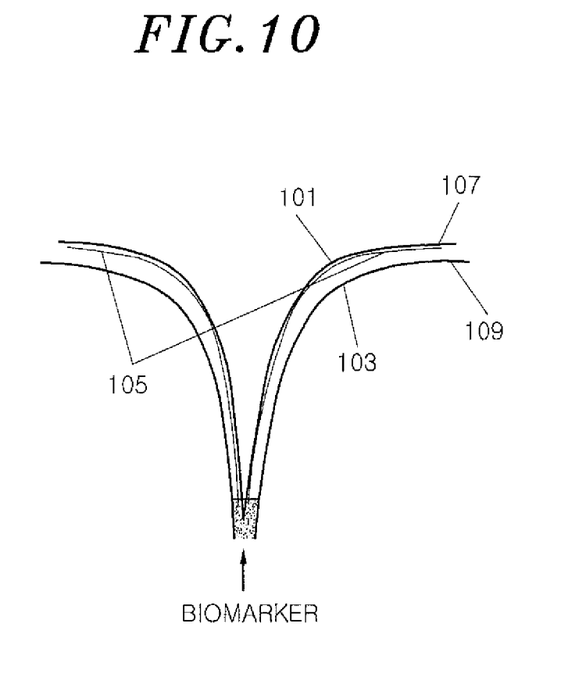
FIG. 10 is a schematic view illustrating a biosensor using the overlapped microneedle structure.

FIG. 10 is a schematic diagram illustrating a biosensor using the overlapped microneedle structure. A biosensor in accordance with an embodiment of the present invention includes: an internal microneedle 101 that is a hollow or solid microneedle; an external hollow microneedle 103 that is disposed at the outside of the internal microneedle 101, has the same surface curve as that of the internal microneedle 101, is spaced apart by a certain distance from a surface of the internal microneedle 101, and surrounds the surface of the internal microneedle 101; an insulator 105 that is coated on an outer surface of the internal microneedle 101; a positive terminal 107 that is connected to a distal end of the internal microneedle 101; a negative terminal 109 that is connected to a distal end of the external microneedle 103; and a measurement device (not shown) that measures a resistance, a current, or a voltage which is generated by a power source. The insulator 105 may be coated on an inner surface of the external microneedle 103.

To manufacture the biosensor, a constant manufacturing condition is first fixed for manufacturing an overlapped microneedle, and thus, two hollow microstructures having the same external appearance are manufactured. Parylene (KISCO, diX N in Japan) is chemical-vapor-deposited (CVD) on a surface of a microneedle, used as an internal microneedle, according to protocol of a manufacturer. Subsequently, as in the embodiment 9, the other internal microneedle is inserted into an external microneedle, thereby establishing an overlapped microneedle structure. A positive power source and a negative power source are connected to respective distal ends of the internal microneedle and external microneedle of the overlapped microneedle structure, and a voltmeter and an ohmmeter (Yokogawa 3201 tester, Japan) are connected to the overlapped microneedle structure (see FIG. 10). In accordance with the present invention, when the overlapped microneedle of the present invention is implanted into skin and connected to the power source, by measuring a resistance value generated by the power source, a meridian point can be found, and a resistance value which is changed due to the change in a health state can be continuously measured.

Furthermore, the inventors adheres a biomarker such as glucose oxidase (GOx) to a distal end in an upper portion of the overlapped microneedle, thereby manufacturing a biosensor for measuring blood glucose contents of a body.

Accordingly, the present invention directly implants the hollow microneedle into skin without collecting blood of a patient, thus enabling the measurement of blood sugar reacting with interstitial fluid (ISF) without fear of pain and blood collection.

While the invention has been shown and described with respect to the embodiments, the present invention is not limited thereto. It will be understood by those skilled in the art that various changes and modifications may be made without departing from the scope of the invention as defined in the following claims.

The invention claimed is:

1. A method for manufacturing a hollow microneedle having a varied appearance, comprising:
    coating a solution of a viscous material on a surface of a substrate;
    bringing the solution of the viscous material into contact with a frame;
    lifting the substrate, the frame, or the substrate and the frame for the contacted frame and substrate to be spaced apart from each other to thereby manufacture a solid microstructure;
    obtaining a bent microneedle structure by sending wind of 5 μm/s to 10 μm/s in a specific direction before the solid microstructure which is manufactured in said lifting the substrate, the frame, or the substrate and the frame is hardened;
    depositing metal on the bent microneedle structure;
    protecting an upper portion of the metal-deposited microneedle structure, and plating metal on a surface of the microneedle structure;
    removing the microneedle structure to obtain a hollow microneedle,
    wherein a coating thickness of the viscous material, a diameter of the frame, a temperature of the viscous material, a lifting speed, a plating thickness, or combination thereof is adjusted.

2. The method of claim 1, wherein in said coating a solution of a viscous material, the viscous material is a polymer compound which is removed by an organic solvent.

3. The method of claim 2, wherein the polymer compound is one of acrylonitrile styrene (AS), polyamide, polyethylene, polyester, polyacryl, polyacetylene, styrene, teflon, polyvinyl chloride, polyurethane, nylon, sulfonic resin, or and epoxy polymer.

4. The method of claim 1, wherein the temperature of the viscous material is adjusted within a range larger than a glass transition temperature and smaller than 120° C., thereby adjusting viscosity of the viscous material.

5. The method of claim 1, wherein multiplication of a lifting speed (μm/s) and lifting time (s) of the substrate, frame, or substrate and frame is adjusted within a range from 500 μm to 5,000 μm.

6. The method of claim 1, wherein said depositing metal on the microneedle structure is performed such that stainless steel, Al, Cr, Ni, Au, Ag, Cu, Ti, Co, or an alloy thereof is deposited on the solid microstructure microneedle structure.

7. The method of claim 6, wherein said depositing metal on the microneedle structure is performed such Ag is chemical-vapor-deposited on the microneedle structure in a silver mirror reaction, or Ag is physical-vapor-deposited on the microneedle structure using sputtering.

8. The method of claim 1, wherein in said protecting an upper portion of the metal-deposited microneedle structure, and plating metal on a surface of the microstructure,
    the plating thickness is adjusted within a range from 10 μm to 50 μm, and
    the plating metal is stainless steel, Al, Cr, Ni, Au, Ag, Cu, Ti, Co, or an alloy thereof.

9. The method of claim 1, wherein an upper portion of the manufactured hollow microneedle is cut by adjusting a bevel angle within a range from 0 degrees to 60 degrees.

10. The method of claim 1, wherein the hollow microneedle is a single hollow microneedle that is connected to an upper portion of a hollow injector.

11. The method of claim 1, wherein the adjusted external appearance of the hollow microneedle is at least one appearance factor selected from a group consisting of an effective length, an internal diameter and external diameter of an upper portion, a diameter, hardness, sharpness, bevel angle, and aspect ratio of a lower portion, a degree of bending, and a bending position.

12. The method of claim 1, wherein in the hollow microneedle, a relationship between an effective length, the lifting speed, a diameter of the lifting frame, and the coating thickness of the viscous material is expressed as an equation $$Y=6000/(x-b)1/2$$

where Y denotes the effective length (μm) of the hollow microneedle, x denotes the internal diameter (μm) of the hollow microneedle, and b denotes "(diameter (μm) of lifting frame+coating thickness (μm) of viscous material)/50".

13. The method of claim 1, wherein the adjusted external appearance of the hollow microneedle is at least one appearance factor selected from a group consisting of an effective length, an internal diameter and external diameter of an upper portion, a diameter, hardness, sharpness, bevel angle, and aspect ratio of a lower portion, a degree of bending, and a bending position.

* * * * *